United States Patent
Thistle

(10) Patent No.: US 10,149,785 B2
(45) Date of Patent: Dec. 11, 2018

(54) DEVICE AND METHOD FOR TREPHINE ALIGNMENT

(71) Applicant: Kyle Thistle, Cambridge, MA (US)

(72) Inventor: Kyle Thistle, Cambridge, MA (US)

(*) Notice: Subject to any disclaimer, the term of this patent is extended or adjusted under 35 U.S.C. 154(b) by 124 days.

(21) Appl. No.: 15/137,656

(22) Filed: Apr. 25, 2016

(65) Prior Publication Data
US 2017/0189234 A1    Jul. 6, 2017

Related U.S. Application Data

(60) Provisional application No. 62/274,371, filed on Jan. 4, 2016.

(51) Int. Cl.
| | |
|---|---|
| *A61F 9/013* | (2006.01) |
| *A61B 17/3205* | (2006.01) |
| *A61B 90/00* | (2016.01) |

(52) U.S. Cl.
CPC ...... *A61F 9/0133* (2013.01); *A61B 17/32053* (2013.01); *A61B 2090/395* (2016.02)

(58) Field of Classification Search
CPC ........ A61F 9/0133; A61F 9/007; A61F 9/013; A61F 9/00736; A61F 9/00; A61F 9/0008; A61B 17/1695; A61B 17/32053; A61B 17/326
See application file for complete search history.

(56) References Cited

U.S. PATENT DOCUMENTS

| | | | |
|---|---|---|---|
| 4,319,575 | A | 3/1982 | Bonte |
| 4,429,696 | A | 2/1984 | Hanna |
| 4,875,767 | A | 10/1989 | Wright |
| 5,578,049 | A | 11/1996 | Feaster |

(Continued)

FOREIGN PATENT DOCUMENTS

| | | |
|---|---|---|
| CN | 102846429 A | 1/2013 |
| FR | 2693368 A1 | 1/1994 |

(Continued)

OTHER PUBLICATIONS

English machine translation of CN102846429, Xu et al., dated Jan. 2, 2013.*

*Primary Examiner* — Todd Scherbel
*Assistant Examiner* — Brooke Labranche
(74) *Attorney, Agent, or Firm* — AKC Patents, LLC

(57) ABSTRACT

A device for holding and aligning a trephine blade includes an elongated cylindrical component, a first alignment structure and a second alignment structure. The elongated cylindrical component extends along a first axis and comprises a hollow cylinder having an open proximal end, an open distal end, an inner cylindrical surface and an outer cylindrical surface. The first alignment structure is integral and co-planar with the proximal end and comprises a first circle attached to the inner cylindrical surface with one or more radially extending rods. The second alignment structure is arranged parallel to the first alignment structure within the hollow cylinder above the distal end and comprises a second circle attached to the inner cylindrical surface with one or more radially extending rods. The first and second circles are coaxial with the first axis and the first circle comprises a diameter that is greater than a diameter of the second circle.

20 Claims, 4 Drawing Sheets

(56) References Cited

U.S. PATENT DOCUMENTS

| | | | |
|---|---|---|---|
| 5,697,945 A * | 12/1997 | Kritzinger | A61F 9/00802 606/161 |
| 6,632,232 B1 * | 10/2003 | Loomas | A61F 2/147 30/301 |
| 2006/0287663 A1 * | 12/2006 | Gayheart | A61F 9/0133 606/166 |
| 2014/0012295 A1 * | 1/2014 | Muraine | A61F 9/0133 606/166 |

FOREIGN PATENT DOCUMENTS

| | | |
|---|---|---|
| GB | 620103 | 3/1949 |
| JP | S54127185 A | 10/1979 |
| SU | 1107858 A | 8/1984 |

* cited by examiner

DEVICE AND METHOD FOR TREPHINE ALIGNMENT

CROSS REFERENCE TO RELATED CO-PENDING APPLICATIONS

This application claims the benefit of U.S. provisional application Ser. No. 62/274,371 filed on Jan. 4, 2016 and entitled Trephine Alignment Device, the contents of which are expressly incorporated herein by reference.

FIELD OF THE INVENTION

The present invention relates to a device and a method for trephine alignment and in particular to a device for an ocular trephine alignment.

BACKGROUND OF THE INVENTION

The present invention relates to medical devices, and specifically to surgical instruments with blades or "trephines." A trephine is a surgical instrument with a cylindrical blade that is commonly used in medical procedures to create a circular incision around an area of interest. A trephine usually includes a hollow metal cylinder with one end of the cylinder having a sharp incising edge. Trephines are also used during ophthalmic surgery in order to correct a corneal defect of a living patient. Radial keratotomy, astigmatic keratotomy, penetrating keratoplasty, and lamellar keratoplasty are common surgical procedures that are known to utilize a trephine. Trephines are also used in corneal transplantation and in cadaveric surgical cornea recovery procedures.

Radial and astigmatic keratotomies are refractive surgeries where the surgeon attempts to correct a patient's corneal curvature. In this procedure, the surgeon first determines the optical zone or specific portion of the cornea which is to remain uncut. Determining and marking this portion of the cornea is typically accomplished by using a trephine and/or specific dyes. When the trephine incising edge is pressed onto the corneal epithelial surface of a patient, it produces a visible imprint on the cornea that encircles and marks the cornea optical zone. The trephine edge can also be coated with marking ink which leaves an ink imprint on the cornea surface when pressed against the corneal epithelial tissue. In radial keratotomy and astigmatic keratotomy a blade is used to create precise incisions on the surface of the cornea outside the marked optical zone. Through specific incisions on the corneal tissue of the patient, the surgeon can modify and correct the corneal curvature.

In a corneal transplantation procedure, a surgeon replaces all or part of a patient's diseased or damaged cornea with donated cadaveric corneal tissue. Penetrating keratoplasty is the procedure in which all layers of the living patient's cornea are replaced and lamellar keratoplasty is the procedure in which a portion or layer of a living patient's cornea is replaced. In keratoplasty procedures the center of the diseased or damaged portion of the cornea is marked through the use of dyes or by pressing or incising the cornea. The surgeon places a trephine over the center of the marked cornea and creates a circular incision on the corneal tissue. The diameter of the trephine is typically under 10.00 mm and will vary depending on the extent of the damaged or diseased area of the cornea. The surgeon removes the diseased or damaged portion of corneal tissue and replaces it with healthy donor cornea tissue by sewing it in place with sutures to the patient's remaining corneal tissue.

In refractive eye surgery and corneal transplantation surgery, trained physicians utilize a combination of resources including microscopes, vacuum suction, specific dyes, blades, and smaller trephine diameter sizes in order to mark areas of a living patient's corneal tissue and stabilize their devices. Several types of devices have been proposed to hold a variety of different trephine diameters. For example, U.S. Pat. Nos. 4,319,575 and 4,429,696 are both multi-part devices that provide different diameter trephine blades by modifying the trephine blades to have an interior shoulder, outward radial arm projections and/or screw threads. Other patents have attempted to describe ways to align their device over a specific area of the eye to assist in refractive surgery and keratoplasty procedures. U.S. Pat. No. 6,632,232 and CN patent 102846429A utilize a single reticle or crosshair design to assist with alignment. While a single crosshair still requires the user to estimate the center of the patient's eye, some devices attempt to minimize this problem by utilizing a combination of microscopes, dyes, and/or physically marking the cornea prior or during the placement of the device to assist with the alignment. Other devices include U.S. Pat. No. 4,875,767 which proposes a device with sliding opaque disks with pinholes that obscures other portions of the eye while allowing the user to visualize the patient's fovea and physically mark the center of the cornea epithelium. U.S. Pat. No. 5,578,049 is a metal device that discloses two levels of overlapping indicator pointers used in conjunction with a microscope to estimate the center of the pupil. Although the overlapping indicator pointers may be useful at a number of distances, they may prove problematic the closer the user's vision approaches the top pointer, as it would obscure the bottom pointer.

Cadaveric surgical cornea recoveries are typically performed by a tissue surgical recovery technician employed by a tissue bank. Tissue banks do not have the same resources that are available to hospitals and tissue recovery technicians are minimally trained compared to the rigorous instruction that physicians receive. The cadaveric surgical cornea recovery takes place in a variety of environments. While the optimal environment is an operating room, cadaveric surgical cornea recoveries also take place in morgue anterooms, pathology suites, and funeral homes. In a cadaveric surgical cornea recovery, a tissue recovery technician typically uses a larger diameter 18.00 mm sterile metal trephine. The larger diameter trephine is utilized to avoid contact with the corneal tissue and to create a circular incision on the sclera of the donor's eye. As a sterile procedure, the technician applies pressure to the speculum with one hand in order to stabilize the donor's eye and maintain eyelid separation. The technician utilizes their free hand to manually place the trephine over the center of the eye or pupil and manually rotates the trephine to create a circular incision on the sclera of the eye. The goal is to avoid any contact with the corneal tissue and to create a circular incision around the center of the eye, resulting in a specific uniform scleral width or scleral rim size. The scleral rim size is a determinant if the corneal tissue can be later processed for transplantation. If the scleral rim size is too small or too large in diameter, the tissue cannot be processed and utilized in keratoplasty surgeries for living patients. Additionally, if the corneal tissue is contacted during the procedure this may result in corneal epithelial damage that may render the tissue unusable for transplant. Placement of the larger diameter trephine on the sclera of the donor cadaver eye is estimated by the tissue recovery technician, resulting in inaccuracy that may render the surgically recovered cadaveric corneal tissue non-viable for transplant.

It would be desirable to have a device and a method that provides a reproducible and accurate alignment of a trephine over an eye in order to extract intact and unmarked corneal tissue with uniform scleral width of specific dimensions.

SUMMARY OF THE INVENTION

The present invention relates to a device and a method that provides a reproducible and accurate alignment of a trephine over an eye in order to extract intact and unmarked corneal tissue with uniform scleral width of specific dimensions.

In general, one aspect of the invention provides a device for holding and aligning a trephine blade including an elongated cylindrical component extending along a first axis and comprising a hollow cylinder having an open proximal end, an open distal end, an inner cylindrical surface and an outer cylindrical surface. The device further includes a first alignment structure and a second alignment structure. The first alignment structure is integral and co-planar with the proximal end and comprises a first circle attached to the inner cylindrical surface with one or more radially extending rods. The second alignment structure is arranged parallel to the first alignment structure within the hollow cylinder above the distal end and comprises a second circle attached to the inner cylindrical surface with one or more radially extending rods. The first and second circles are coaxial with the first axis and the first circle comprises a diameter that is greater than a diameter of the second circle.

Implementations of this aspect of the invention include the following. One of the radially extending rods of the second alignment structure comprises a free end that extends to a center of the second circle. The second circle comprises a diameter larger than a diameter of an object upon which the device is centered. The second circle comprises a diameter in the range of 6 mm to 8 mm, and the first circle comprises a diameter in the range of 8 mm to 10 mm. The hollow cylinder comprises one or more elongated openings extending along the first axis and being configured to allow light to pass through from the outside of the hollow cylinder into the inside of the hollow cylinder. The hollow cylinder comprises one or more apertures arranged near the distal end and being configured to allow light to pass through from the outside of the hollow cylinder into the inside of the hollow cylinder. The device further includes one or more inward extending steps formed in the inner cylindrical surface above the open distal end and below the second alignment structure and the one or more steps are shaped and dimensioned to level and frictionally support a non-cutting edge of one or more trephine blades with different diameters. A non-cutting edge of a trephine blade is removably attached to the distal end. The cylindrical component comprises plastic or other material that can be sterilized and provides sufficient friction for finger placement, manipulation of the device, and trephine attachment.

In general, in another aspect, the invention provides a method for holding and aligning a trephine blade including the following: First, providing an elongated cylindrical component extending along a first axis and comprising a hollow cylinder having an open proximal end, an open distal end, an inner cylindrical surface and an outer cylindrical surface. Next, providing a first alignment structure being integral and co-planar with the proximal end and comprising a first circle attached to the inner cylindrical surface with one or more radially extending rods. Next, providing a second alignment structure arranged parallel to the first alignment structure within the hollow cylinder above the distal end and comprising a second circle attached to the inner cylindrical surface with one or more radially extending rods. Next, attaching a trephine blade to the distal end of the elongated component. The first and second circles are coaxial with the first axis and the first circle comprises a diameter that is greater than a diameter of the second circle.

Among the advantages of the invention may be one or more of the following. Previous methods of surgically recovering cadaveric corneal tissue for transplant rely on the technician approximating trephine placement over the center of the eye or pupil, while avoiding contact with the cornea and rotating the trephine with one hand to create a circular incision on the sclera of the eye. The device of the present invention attaches to the trephine in order to assist in the proper alignment of the trephine during the incision procedure and other surgical procedures that require specific trephine placement. The device of the present invention fits trephines of different lengths and diameters, extends from the body of the trephine to provide an improved area for the user to hold and manipulate the trephine, facilitates ambient light to illuminate the trephine incising edge, provides a means for the user to visually confirm trephine fit and incorporates one or more visual reference structures. The device of the present invention reduces human error during trephine placement and trephine manipulation.

BRIEF DESCRIPTION OF THE DRAWINGS

Referring to the figures, wherein like numerals represent like parts throughout the several views.

DETAILED DESCRIPTION OF THE INVENTION

Figure 1:
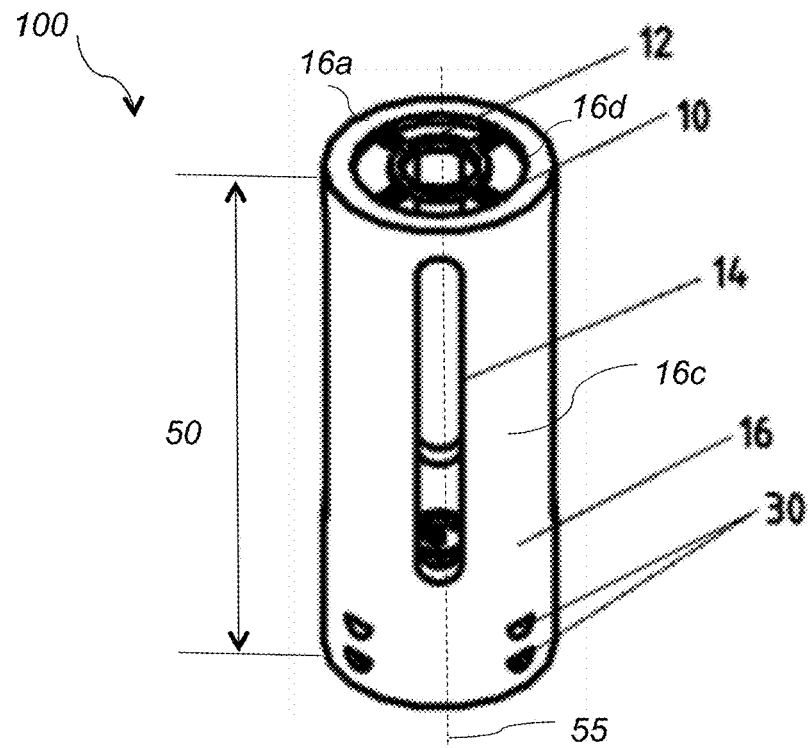
FIG. 1 is a perspective view of a trephine alignment device constructed in accordance with one embodiment of the invention, showing the front and top of the device.
Figure 2:
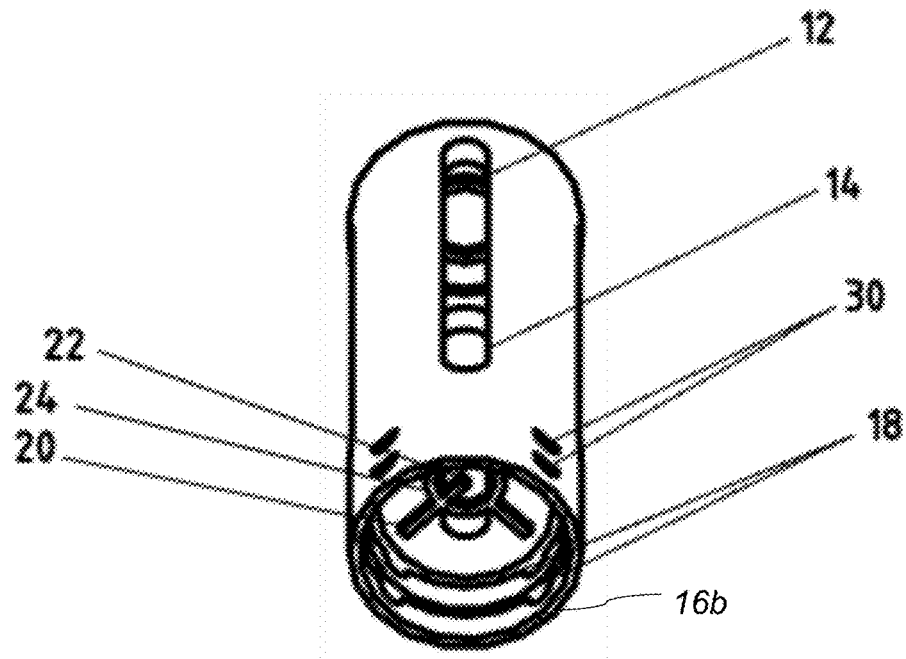
FIG. 2 is a perspective view of the trephine alignment device of FIG. 1, showing the front and bottom of the device.

Referring to FIG. 1 and FIG. 2, a trephine alignment device 100 includes an elongated hollow cylindrical body 16 extending along axis 55 and having an open proximal end (top end) 16a, an open distal end (bottom end) 16b, a cylindrical outer surface 16c, and a cylindrical inner surface 16d. The hollow cylindrical body 16 has an appropriate length and width for allowing multiple finger placement, manual manipulation, and visual alignment. In one example, body 16 has a length 50 of 58 mm, an outer diameter 52 of 23.4 mm, and a body thickness at the top end of 3 mm. In another example, the body thickness at the bottom end is reduced by about 1 mm to incorporate trephines of different diameters, as will be described below. In one example, the body 16 is dimensioned to incorporate an 18 mm trephine and a 19.5 mm trephine. The 18 mm trephine has an outer diameter of 19.6 mm and the 19.5 mm trephine has an outer diameter of 21.1 mm. The body 16 is made of plastic or other material that can be sterilized and provides sufficient friction for finger placement, device manipulation, and trephine attachment. The body 16, as shown in FIG. 1 is cylindrical, which facilitates rotational manipulation and trephine attachment. In other embodiments, opened and closed shapes other than cylindrical, such as triangular, polygonal, square, octagonal, hexagonal, and combinations thereof, among others, are used. In other embodiments, a bearing is used to allow for rotational control and trephine attachment.

Figure 5:
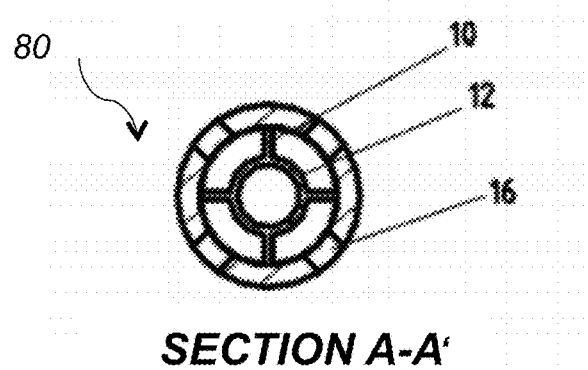
FIG. 5 is a horizontal cross-sectional view of the trephine alignment device of FIG. 1 along A-A' plane, shown in FIG. 3.

The top end 16a of the device 100 includes a visual reference structure 80 that is composed of a top inner circle 12 connected to the inside surface 16d of the body 16 with four rods 10, as shown in FIG. 5. The center of the top inner circle 12 is the center of the device. In one example, the top inner circle 12 has an inner diameter in the range of 8 mm to 10 mm and the top rods 10 and inner circle 12 have a thickness of 1 mm. The top inner circle 12 and top rods 10 assist in aligning the trephine over the center of the eye, as will be described below. The top reference structure 80 is made out of the same material as the body 16, e.g. plastic, or other sterilizable material.

The front of the body 16 contains one or more apertures 30 and/or openings 14 that allow entrance of ambient light to illuminate the inside of the device and the trephine incising edge. In other embodiments, the body 16 of the device is made of an optically transparent material and in this case openings 14 may not be necessary. In one example, one or more semi-circular apertures 30 are positioned near the bottom 16b of the body 16, as shown in FIG. 1. Apertures 30 allow the user to visually confirm that the trephine is fully inserted and level in the device. In this example, apertures 30 have a diameter of 3.175 mm. In one example, opening 14 has an elongated oval structure that has a length of 39.5 mm and a diameter of 4.5 mm, as shown in FIG. 1. In other embodiments, voids of other shapes and dimensions that increase the interior lighting of the device are used. In some embodiments, an independent light source is added to illuminate the trephine incising edge.

Figures 6, 7:
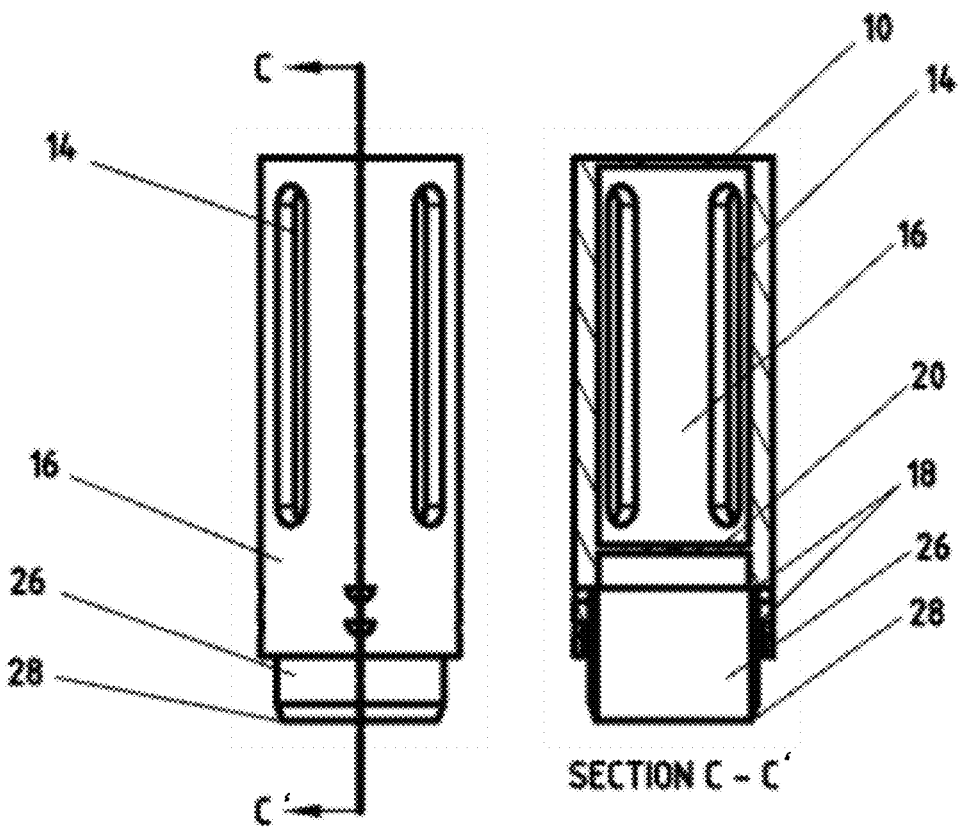
FIG. 6 is a front isomeric view of the trephine alignment device of FIG. 1 with an attached trephine.
FIG. 7 is a lateral cross-sectional view of the trephine alignment device of FIG. 6, along plane C-C'.

Referring to FIG. 2, the bottom end 16b of the device 100 includes in the interior surface 16d different levels or steps 18. Each step 18 is designed to fit a different size diameter trephine 26, getting incrementally smaller in diameter deeper into the device, as shown in FIG. 2 and FIG. 7. The trephine 26 slides into its appropriate step 18 and stops when it meets the next smaller step 18. The trephine 26 is secured within the device 100 through friction between the outer surface of the trephine 26 and the interior surface of the device 16d, and the trephine 26 is level when in contact with the next smaller step. In this example, the friction between the trephine 26 and interior surface of the device 16d is also of a magnitude that would allow the user to remove the trephine 26 from the device 100. Multiple steps 18 are formed on the interior surface 16d of the bottom end 16b of the device 100 to fit various trephine sizes if the trephine is secured within the device. In other embodiments, multiple steps 18 are formed on the exterior surface 16c of the bottom end 16b of the device 100 so that the trephine 16 is secured on the outside of the device. Other variations for securing different size diameter trephines 26 include adding magnetic material to the bottom of the device 100, sloping the interior or exterior bottom of the trephine alignment device, creating elastic attachment arms on the device, creating concentric channels in the thickness of the body 16 in the bottom of the device or modifying the design of the trephine to mechanically secure to the device via structures such as screwthreads.

Figure 4:
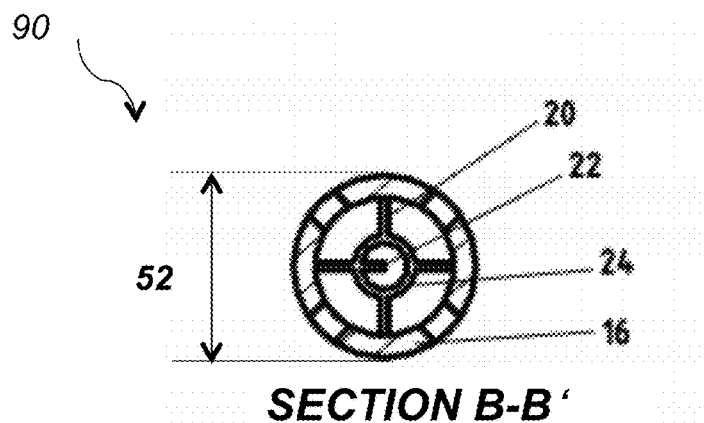
FIG. 4 is a horizontal cross-sectional view of the trephine alignment device of FIG. 1 along B-B' plane, shown in FIG. 3.
Figure 3:
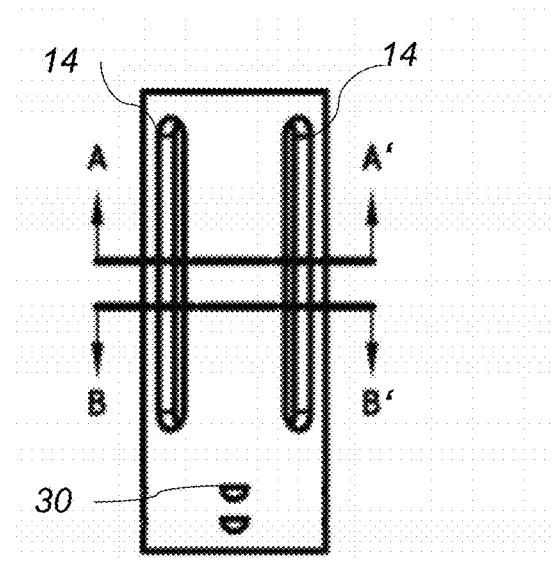
FIG. 3 is a front isomeric view of the trephine alignment device of FIG. 1.

FIG. 3 is a front view of the trephine alignment device 100 showing two openings 14 and demonstrating the horizontal cross-sectional view along plane B-B' from the middle of the device towards the bottom of the device, shown in FIG. 4, and the horizontal cross-sectional view along plane A-A' from the middle of the device towards the top of the device, shown in FIG. 5.

Referring to FIG. 4, in one embodiment, the bottom half of the device 100 includes a second visual reference structure 90 composed of a bottom inner circle 24 connected to the inside surface 16d of the body 16 with four bottom rods 20. The center of the bottom inner circle 24 is the center of the device 100. One of the rods 22 extends halfway into the bottom inner circle 24 and the free end of the extended rod 22 marks the center of the inner circle 24. The bottom inner circle 24, bottom rods 20, and the extended rod 22 assist in aligning the trephine over the center of the eye, as will be described below. In one example, the bottom inner circle 24 has an inner diameter in the range of 6 mm to 8 mm, an inner circle thickness and a rod thickness of 1 mm and the extended rod 22 extends to the center of the bottom inner circle 24. The bottom reference structure 90 is made out of the same material as the body 16, e.g. plastic, or other sterilizable materials.

Figure 10:
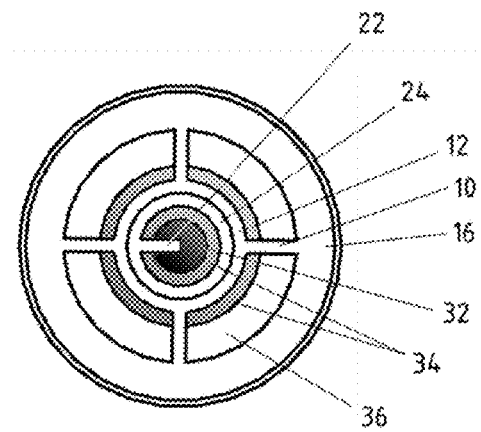
FIG. 10 is a top view of the assembly of FIG. 9.

FIG. 10 is a top view of the trephine alignment device 100 with an attached trephine in contact with the sclera of the eye, showing the line of sight down the device through the top visual reference structure 80 and bottom visual reference structure 90. The top inner circle 12, top rods 10, bottom inner circle 24, and extended rod 22 are visualized. The top inner circle 12 is larger in diameter than the bottom inner circle 24. The bottom inner circle 24 is larger in diameter than the average cadaveric human pupil diameter. Typical human eye dimensions include a pupil diameter of 4 mm, iris diameter of 12 mm and globe diameter of 24 mm.

Figure 8:
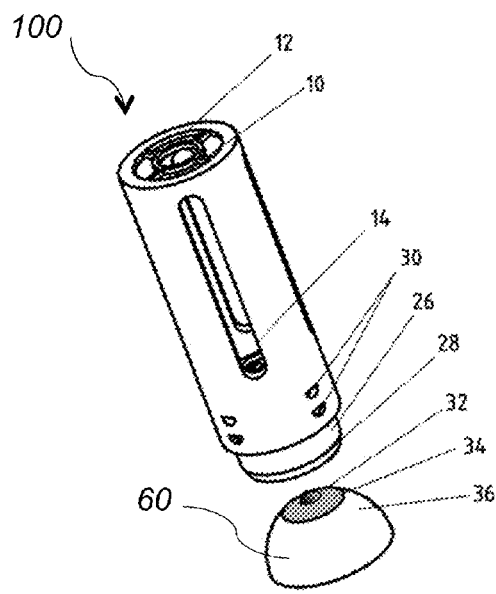
FIG. 8 is a perspective view of an assembly depicting the trephine alignment device of FIG. 1 with an attached trephine positioned above an eye.

Referring to FIG. 8, when device 100 is aligned over the center of the eye 60, the pupil 32 is centered within the bottom inner circle 24, the extended rod 22 marks the center of the pupil, and the bottom inner circle 24 is centered within the top inner circle 12. By aligning the top visual reference structure 80, the bottom visual reference structure 90, and pupil 32, the trephine is placed accurately over the eye 60, as shown in FIG. 10. In this embodiment circles 12 and 24 are components of the top visual reference structure 80 and bottom reference structure 90, respectively. In other embodiments other open or closed shapes, dimensions, and/or number of visual reference structures are used in order to assist in creating an aligned line of sight.

FIG. 6 is a front view of the trephine alignment device 100 with an attached trephine 26 having a trephine incising edge 28. FIG. 7 is a lateral cross-sectional view of the trephine alignment device 100 along plane C-C' showing the trephine 26 placement within the stepped bottom end 16b of device 100. In this example, the interior of the bottom 16b of the device 100 contains different levels or steps 18. Each step 18 is designed to fit a different size trephine, getting incrementally smaller deeper in the device, as was mentioned above. In this embodiment, the trephine alignment device 100 is a separate piece from the trephine 26. In other embodiments, the trephine alignment device 100 is manufactured with an integrated trephine 26 as one piece.

Other embodiments of the trephine alignment device 100 include one or more of the following. The trephine 26 includes holes throughout the trephine body and a wire or other material is threaded through the holes to create a number of visual reference structures. More than two reference visual structures are used. The visual reference structures may be open or closed structures that include non-circular shapes, such as rectangular, triangular, polygonal, hexagonal, or combinations thereof, among others. The top visual reference structure 80 may have a diameter that is smaller than the diameter of the bottom visual reference structure 90. The diameter of the bottom visual reference structure 90 may be smaller than the area it encircles, such as the eye or the pupil 32. In yet other embodiments, the top visual reference structure 80 includes the extended rod 22.

Figure 9:
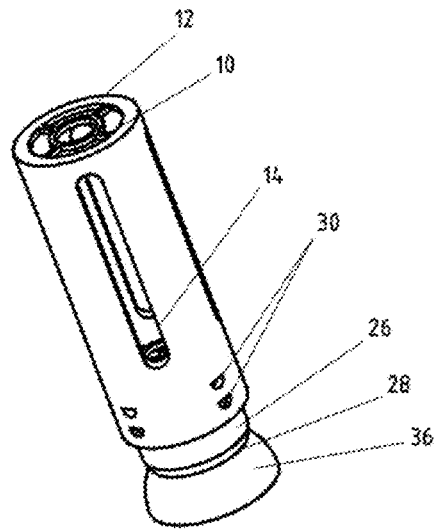
FIG. 9 is a perspective view of the assembly of FIG. 8 depicting the trephine alignment device positioned in contact with the eye.

In operation, one uses the trephine alignment device 100 by inserting the trephine 26 into the bottom 16*b* of the device. The device 100 secures and levels the trephine 26 in the appropriate step 18 and the user visually confirms that the trephine 26 is fully inserted and level in the device through the apertures 30 before placing the trephine on the eye 60, as shown in FIG. 8. Once the trephine 26 is secured in place, the user places the device 100 with the attached trephine over the eye 60 for the surgical corneal recovery procedure, as shown in FIG. 9. The user looks down the device 100 to align the trephine 26 over the center of the eye or pupil 32. The top inner circle 12 is larger in diameter than the bottom inner circle 24. The bottom inner circle 24 is larger in diameter than the average human pupil 32. When aligned over the center of the eye 60, the pupil 32 is centered within the bottom inner circle 24 with the extended rod 22 marking the center of the pupil, and the bottom inner circle 24 is centered within the top inner circle 12. When the top visual reference structure 80, bottom visual reference structure 90, and pupil 32 are aligned, the trephine 26 is at the center of the eye 60. When the device 100 is aligned and the trephine incising edge 28 is in contact with the sclera 36 of the eye, the user rotates the trephine alignment device 100 to create a circular incision on the sclera 36.

Among the advantages of the invention may be one or more of the following. One embodiment attaches to and levels a variety of trephine lengths and diameter sizes, including larger 18.00 mm diameter trephines without requiring the modification of the trephine. One embodiment elongates the holding area of the trephine which provides an improved area for the user to hold and manipulate the trephine, and allows the user to operate the device with one hand if necessary, such as a cadaveric surgical recovery procedure. One embodiment provides a generally open view through the device that allows the user to visualize different eye structures, such as the pupil, iris, and sclera. One embodiment facilitates ambient light from the environment to illuminate the incising edge of the trephine and other eye structures such as the pupil, iris, and sclera. One embodiment provides a means for the user to visually confirm trephine fit in the device. One embodiment comprises one or more alignment structures that assist in the proper alignment of the trephine over the center of the eye and allow the user to get as close to the device as needed without the alignment structures becoming obscured. One embodiment is made of a sterilizable plastic or polymer and would be less expensive to manufacture in one or multiple parts when compared to other materials, which would be beneficial to organizations concerned with cost effectiveness and/or limited resources such as organ and tissue banks. One embodiment is designed for users with limited training and resources available, and does not require microscopes, dyes, suction, etc. that other ophthalmic procedures utilize. One embodiment assists in creating accurate incisions on the sclera of the eye while avoiding contact with the corneal tissue.

As described, the trephine alignment device 100 provides a reproducible and accurate alignment of a trephine over an eye in order to extract intact and unmarked corneal tissue with uniform scleral width of specific dimensions. The trephine alignment device 100 may also be useful for any procedure utilizing a trephine that requires accurate placement and manipulation.

Several embodiments of the present invention have been described. Nevertheless, it will be understood that various modifications may be made without departing from the spirit and scope of the invention. Accordingly, other embodiments are within the scope of the following claims.

What is claimed is:

1. A device for holding and aligning a trephine blade comprising:
   an elongated cylindrical component extending along a first axis and comprising a hollow cylinder having an open proximal end, an open distal end, an inner cylindrical surface and an outer cylindrical surface;
   a first alignment structure being integral and co-planar with the proximal end and comprising a first circle located within the proximal end of the hollow cylinder and being attached to the inner cylindrical surface of the hollow cylinder with one or more rods extending radially from the first circle towards the inner cylindrical surface of the hollow cylinder;
   a second alignment structure arranged parallel to the first alignment structure within the hollow cylinder above the distal end and comprising a second circle located within the hollow cylinder above the distal end and being integral with and attached to the inner cylindrical surface with one or more rods extending radially from the second circle towards the inner cylindrical surface of the hollow cylinder; and
   wherein the first and second circles are coaxial with the first axis.

2. The device of claim 1, wherein the first circle comprises a diameter that is greater than a diameter of the second circle.

3. The device of claim 1, wherein one of the radially extending rods of the second alignment structure comprises a free end that extends to a center of the second circle.

4. The device of claim 1, wherein the second circle comprises a diameter larger than a diameter of an object upon which the device is centered.

5. The device of claim 1, wherein the second circle comprises a diameter in the range of 6 mm to 8 mm, and wherein the first circle comprises a diameter in the range of 8 mm to 10 mm.

6. The device of claim 1, wherein the hollow cylinder comprises one or more elongated openings extending along the first axis and being configured to allow light to pass through from outside of the hollow cylinder into the inside of the hollow cylinder.

7. The device of claim 1, wherein the hollow cylinder comprises one or more apertures arranged near the distal end and being configured to allow light to pass through from outside of the hollow cylinder into the inside of the hollow cylinder.

8. The device of claim 1, further comprising one or more inward extending steps formed in the inner cylindrical surface above the open distal end and below the second alignment structure and wherein the one or more steps are shaped and dimensioned to level and frictionally support a non-cutting edge of one or more trephine blades with different diameters.

9. The device of claim 1, wherein a non-cutting edge of a trephine blade is removably attached to the distal end.

10. The device of claim 1, wherein the cylindrical component comprises plastic or other material that can be sterilized and provides sufficient friction for finger placement, manipulation of the device, and trephine attachment.

11. A method for holding and aligning a trephine blade comprising:
    providing an elongated cylindrical component extending along a first axis and comprising a hollow cylinder having an open proximal end, an open distal end, an inner cylindrical surface and an outer cylindrical surface;
    providing a first alignment structure being integral and co-planar with the proximal end and comprising a first circle located within the open proximal end of the hollow cylinder and being attached to the inner cylindrical surface of the hollow cylinder with one or more rods extending radially from the first circle towards the inner cylindrical surface of the hollow cylinder;
    providing a second alignment structure arranged parallel to the first alignment structure within the hollow cylinder above the distal end and comprising a second circle located within the hollow cylinder above the distal end and being integral with and attached to the inner cylindrical surface of the hollow cylinder with one or more rods extending radially from the second circle towards the inner cylindrical surface of the hollow cylinder;
    attaching a trephine blade to the distal end of the elongated component;
    wherein the first and second circles are coaxial with the first axis.

12. The method of claim 11, wherein the first circle comprises a diameter that is greater than a diameter of the second circle.

13. The method of claim 11, wherein one of the radially extending rods of the second alignment structure comprises a free end that extends to a center of the second circle.

14. The method of claim 11, wherein the second circle comprises a diameter larger than a diameter of an object upon which the device is centered.

15. The method of claim 11, wherein the second circle comprises a diameter in the range of 6 mm to 8 mm, and wherein the first circle comprises a diameter in the range of 8 mm to 10 mm.

16. The method of claim 11, wherein the hollow cylinder comprises one or more elongated openings extending along the first axis and being configured to allow light to pass through from outside of the hollow cylinder into the inside of the hollow cylinder.

17. The method of claim 11, wherein the hollow cylinder comprises one or more apertures arranged near the distal end and being configured to allow light to pass through from outside of the hollow cylinder into the inside of the hollow cylinder.

18. The method of claim 11, further comprising one or more inward extending steps formed in the inner cylindrical surface above the open distal end and below the second alignment structure and wherein the one or more steps are shaped and dimensioned to level and frictionally support a non-cutting edge of one or more trephine blades with different diameters.

19. The method of claim 11, wherein a non-cutting edge of a trephine blade is removably attached to the distal end.

20. The method of claim 11, wherein the cylindrical component comprises plastic or other material that can be sterilized and provides sufficient friction for finger placement, manipulation of the device, and trephine attachment.

* * * * *